US009884857B2

(12) United States Patent
Hafner et al.

(10) Patent No.: US 9,884,857 B2
(45) Date of Patent: Feb. 6, 2018

(54) SALTS OF DASATINIB IN AMORPHOUS FORM

(71) Applicant: BASF SE, Ludwigshafen (DE)

(72) Inventors: Andreas Hafner, Gelterkinden (CH); Fritz Blatter, Reinach (CH); Martin Szelagiewicz, Basel (CH); Bernd Siebenhaar, Kandern-Wollbach (DE); Tiziana Chiodo, Mannheim (DE); Tobias Hintermann, Therwil (CH); Beate Salvador, Ellerstadt (DE); Marcus Vossen, Limburgerhof (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/906,974

(22) PCT Filed: Jul. 22, 2014

(86) PCT No.: PCT/EP2014/065674
§ 371 (c)(1),
(2) Date: Jan. 22, 2016

(87) PCT Pub. No.: WO2015/011119
PCT Pub. Date: Jan. 29, 2015

(65) Prior Publication Data
US 2016/0168142 A1 Jun. 16, 2016

(30) Foreign Application Priority Data

Jul. 25, 2013 (EP) .................... 13178015

(51) Int. Cl.
C07D 417/12 (2006.01)
C07D 275/06 (2006.01)
C07D 213/80 (2006.01)
C07C 55/12 (2006.01)

(52) U.S. Cl.
CPC ............ C07D 417/12 (2013.01); C07C 55/12 (2013.01); C07D 213/80 (2013.01); C07D 275/06 (2013.01)

(58) Field of Classification Search
CPC .. C07D 417/12; C07D 275/06; C07D 213/80; C07C 55/12
See application file for complete search history.

(56) References Cited

U.S. PATENT DOCUMENTS

| 6,596,746 | B1 | 7/2003 | Das et al. |
| 7,491,725 | B2 | 2/2009 | Lajeunesse et al. |
| 7,973,045 | B2 | 7/2011 | Simo et al. |
| 8,067,423 | B2 | 11/2011 | Simo et al. |
| 8,796,481 | B2 | 8/2014 | Berens et al. |
| 9,199,997 | B2 | 12/2015 | Yamamoto et al. |
| 9,221,789 | B2 | 12/2015 | Chiodo et al. |
| 9,290,452 | B2 | 3/2016 | Hafner et al. |
| 2004/0054186 | A1 | 3/2004 | Das et al. |
| 2006/0004067 | A1 | 1/2006 | Chen et al. |
| 2014/0162989 | A1 | 6/2014 | Zaworotko et al. |
| 2014/0205641 | A1 | 7/2014 | Sowa et al. |
| 2015/0126520 | A1 | 5/2015 | Chiodo et al. |
| 2015/0133463 | A1 | 5/2015 | Chiodo et al. |
| 2015/0246901 | A1 | 9/2015 | Chiodo et al. |
| 2015/0333124 | A1 | 11/2015 | Hintermann et al. |
| 2016/0015034 | A1 | 1/2016 | Bratz et al. |

FOREIGN PATENT DOCUMENTS

| CA | 2555291 C | 1/2017 |
| CN | 102030745 A | 4/2011 |
| JP | 2005519112 A | 6/2005 |
| RU | 2382039 C2 | 2/2010 |
| WO | WO-00/62778 A1 | 10/2000 |
| WO | WO-2007/035874 A1 | 3/2007 |
| WO | WO-2009/053854 A2 | 4/2009 |
| WO | WO-2010/062715 A2 | 6/2010 |
| WO | WO-2010/067374 A2 | 6/2010 |
| WO | WO-2010/081443 A2 | 7/2010 |
| WO | WO-2013/081016 A1 | 6/2013 |

OTHER PUBLICATIONS

Molecular mechanisms of acquired resistance to tyrosine kinase targeted therapy, Sierra et al; licensee BioMed Central Ltd. 2010.*
J.R. Hughey et al., Solid-State Techniques for Improving Solubility in, AAPS Advances in Pharmaceutical Sciences Series (D. Crommelin ed., 2012) ("Hughey").*
U.S. Appl. No. 14/907,148, filed Jan. 22, 2016, Hafner et al.
"Amorphous active pharmaceutical ingredients having special characteristics and methods for their preparation", Research Disclosure, vol. 538, No. 1, pp. 127 (Feb. 1, 2009).
(Continued)

Primary Examiner — Alexander R Pagano
Assistant Examiner — Ebenezer O Sackey
(74) Attorney, Agent, or Firm — Drinker Biddle & Reath LLP

(57) ABSTRACT

The present invention primarily relates to salts of Dasatinib, wherein the salts are in amorphous form. The salts described herein preferably comprise a cation of a compound of formula 1 formula 1

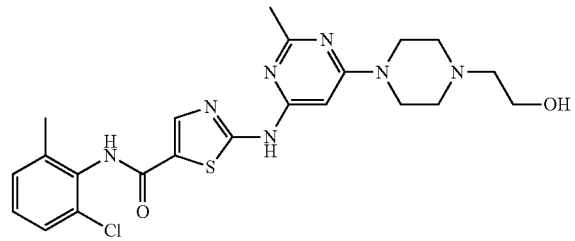

and an anion of a second compound selected from the group consisting of glutaric acid, nicotinic acid and saccharin. The invention is further related to pharmaceutical compositions comprising such a salt. Furthermore, the invention relates to processes for preparing said salts. The invention also relates to several aspects of using said salt or pharmaceutical composition to treat a disease.

18 Claims, 3 Drawing Sheets

(56) References Cited

OTHER PUBLICATIONS

Banerjee, R., et al., "Saccharin Salts of Active Pharmaceutical Ingredients, Their Crystal Structures, and Increased Water Solubilities", Crystal Growth & Design, vol. 5, No. 6, pp. 2299-2309 (Nov. 1, 2005).

Das, J., et al., "2-aminothiazole as a novel kinase inhibitor template. Structure-activity relationship studies toward the discovery of N-(2-Chloro-6-methylphenyl)-2-[{6-[4-(2-hydroxyethyl)-1-piperazinyl)]-2-methyl-4-pyrimidinyl]amino)]-1,3-thiazole-5-carboxamide (Dasatinib, BMS-354825) as a Potent pan-Src Kinase Inhibitor", Journal of Medicinal Chemistry, vol. 49, No. 23, pp. 6819-6832 (Nov. 1, 2006).

European Search Report for EP13178015 dated Sep. 5, 2013.

International Search Report for PCT/EP2014/065674 dated Mar. 31, 2015.

Rodriguez-Spong, B., et al., "General principles of pharmaceutical solid polymorphism: a supramolecular perspective", Advanced Drug Delivery Reviews, vol. 56, No. 3, pp. 241-274 (Feb. 23, 2004).

McNamara, D. P., et al., "Use of a Glutaric Acid Cocrystal to Improve Oral Bioavailability of a Low Solubility API", Pharamceutical Research, 2006, vol. 23, No. 8, pp. 1888-1897.

"Recent Progress in Physicochemical Characterization and Formulation Technologies for Poorly Soluble Drugs", 2010, pp. 213 to 223. Not in English.

"The Practice of Medicinal Chemistry", 1999, vol. 2nd, pp. 347-365. Not in English.

Bauer, J., "Pharmaceutical Solids the Amorphous Phase", Journal of Validation technology, Pharmaceutical Solids. 2009, pp. 63-68.

English Translation of Japanese Office Action for Japanese Patent Application No. 16/528495, dated Jun. 5, 2017.

Journal of the Society of Powder Technology, 1985, Japan, vol. 22, Issue 2, pp. 85-97. Not in English.

Russian Office Action for Application No. 2016106124, dated May 25, 2017.

Australian Office Action for application No. 2014295143, dated Jun. 30, 2016.

\* cited by examiner

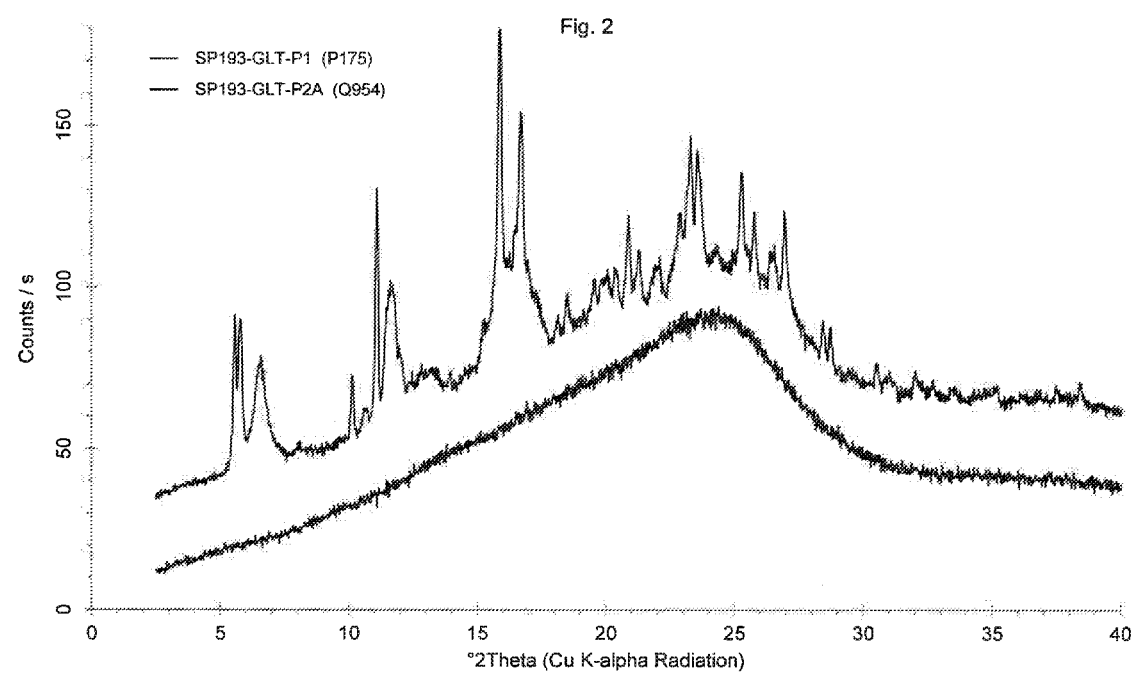

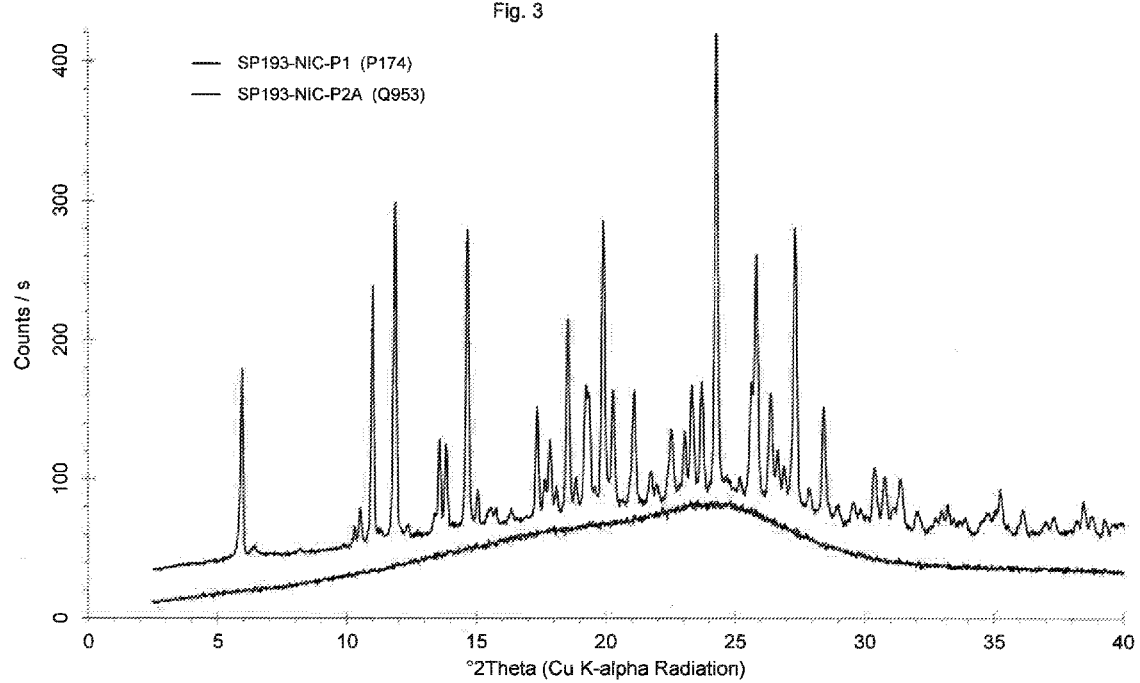

SALTS OF DASATINIB IN AMORPHOUS FORM

CROSS-REFERENCE TO RELATED APPLICATIONS

This application is a national stage application (under 35 U.S.C. §371) of PCT/EP2014/065674, filed Jul. 22, 2014, which claims benefit of European Application No. 13178015.7, filed Jul. 25, 2013, both of which are incorporated herein by reference in their entirety.

Dasatinib which is also known as BMS-354825 was disclosed in WO Patent Publication No. 00/62778 and in U.S. Pat. No. 6,596,746. Dasatinib, chemically N-(2-chloro-6-methylphenyl)-2-[[6-[4-(2-hydroxyethyl)-1-piperazinyl]-2-methyl-4-pyrimidinyl]amino]-5-thiazolecarboxamide, is represented by the following structure:

formula 1

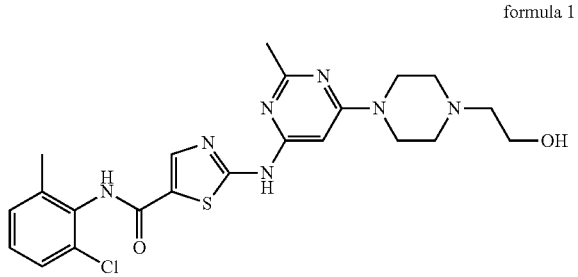 [SMILES: Cc1nc(Nc2ncc(C(=O)Nc3c(C)cccc3Cl)s2)cc(N2CCN(CCO)CC2)n1]

Dasatinib is a drug produced by Bristol-Myers Squibb and sold under the trade name Sprycel® (which contains Dasatinib monohydrate as the active ingredient). Dasatinib is an oral dual BCR/ABL and Src family tyrosine kinase inhibitor approved for use in patients with chronic myelogenous leukemia (CML) after imatinib treatemant and Philadelphia chromosome-positive acute lymphoblastic leukemia (Ph+ ALL).

The present invention primarily relates to a salt of Dasatinib, wherein the salt is in amorphous form. The present amorphous salt of Dasatinib is a solid under standard conditions (300K, atmospheric pressure); it is typically formed with a pharmaceutically acceptable acidic organic compound such as a carboxylic acid or an amide of a sulphonic acid, and generally does not require the presence of further substances such as tectons or complexing agents in order to stabilize the amorphous form and/or prevent crystallization. Preferably, the salt is a salt selected from the group consisting of Dasatinib nicotinate, Dasatinib glutarate and Dasatinib saccharinate.

The invention is further related to pharmaceutical compositions comprising said salt. Furthermore, the invention also relates to processes for preparing said salt. The invention also relates to several aspects of using said salt or pharmaceutical composition to treat a disease. Further details as well as further aspects of the present invention will be described herein below.

Dasatinib is known to exist in close to 60 solid-state forms: a monohydrate, four anhydrous and unsolvated forms which are described in U.S. Pat. No. 7,491,725B2, US2006/0004067A1, U.S. Pat. No. 7,973,045B2, and WO2010/067374, and therein referred to as forms N-6, T1H1-7, B, and I. Further forms (such as 52 solvates) are known from WO2007/035874, US2006/0004067A, WO2009/053854A2, U.S. Pat. No. 8,067,423B, WO2010/062715, and CN102030745. In particular, patent application WO 2010/062715 includes the solvents isosorbide dimethyl ether, N,N'-dimethylethylene urea and N,N'-dimethyl-N,N'-propylene urea. Isosorbide dimethyl ether is used in cosmetic and pharmaceutical formulations.

Some salts of Dasatinib in crystalline form, such as Dasatinib hydrochloride, have been described in WO2007/035874.

WO 2010/081443 proposes certain complexes of tyrosine kinase inhibitors with tectones such as alginic acids, pectins or beta glucan, which may contain the tyrosine kinase inhibitor in form of a salt. Research Disclosure 538 of 1 Feb. 2009 describes on page 127 a general method for obtaining amorphous forms of active ingredients The discovery of new forms of a pharmaceutically useful compound offers an opportunity to improve the performance profile of a pharmaceutical product. It widens the reservoir of materials a formulation scientist has available for designing a new dosage form of a drug with improved characteristics. One of the most important characteristics of an active pharmaceutical ingredient such as Dasatinib is the bioavailability which is often determined by the aqueous solubility.

Existing solid forms of Dasatinib still leave room for improvement of physical as well as biological characteristics, because the aqueous solubility of Dasatinib monohydrate is very poor. There exists a continuing need for providing other, advantageous solid forms of N-(2-chloro-6-methylphenyl)-2-[[6-[4-(2-hydroxyethyl)-1-piperazinyl]-2-methyl-4-pyrimidinyl]amino ]-5-thiazolecarboxamide. Another object is to provide solid forms of Dasatinib to optimize manufacture, formulation, stability, and biological efficiency. Preferably, the new solid forms should show advantages with respect to solubility, lower complexity of their polymorph landscape, in particular a reduced tendency for solvate formation, and/or improved behavior on filtration, drying and crystallization.

SUMMARY OF THE INVENTION

The invention provides a—hitherto not described—salt of Dasatinib in amorphous form, i.e. a solid salt of Dasatinib being substantially free of the crystalline form of Dasatinib or, respectively, not containing any crystalline Dasatinib at all. The amorphous salt of the invention thus typically forms an amorphous phase mainly consisting of cations of a compound of formula 1 (typically the protonated form of Dasatinib) and the second component, which is generally selected from a pharmaceutically acceptable acidic organic compounds such as a carboxylic acid or an amide of a sulphonic acid (typically in the form of its deprotonated anion). In case that any further component is contained in the amorphous salt of the invention, and thus in the amorphous phase containg it, its mass generally is less than the mass of the present amorphous salt; preferably, the total mass of such further component (such as water) or components does not exceed 20% by weight of the total mass of the amorphous phase which comprises the amorphous salt of the invention.

Preferably, such a salt comprises a cation of a compound of formula 1 (INN: Dasatinib)

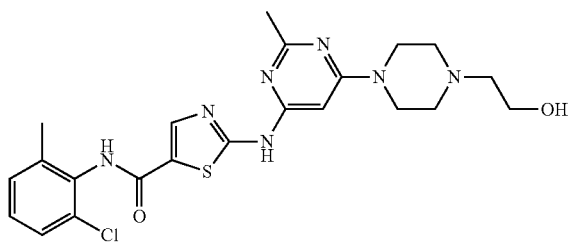

formula 1 and an anion of a second compound selected from the group consisting of glutaric acid, nicotinic acid and saccharin.

Novel pharmaceutical compositions containing these salts and processes for manufacture of such salts as well as aspects of using said salts or compositions to treat a disease are also described herein.

The salt is preferably selected from the group consisting of Dasatinib nicotinate, Dasatinib glutarate and Dasatinib saccharinate, wherein, particularly preferably, the molar ratio of the cation of the compound of formula 1 to the respective counterion is in the range of from 0.5 to 2.0, preferably about 1:1.

The new solid forms of the invention are especially advantageous with respect to improved solubility, high glass transition temperature, good storage stability.

BRIEF DESCRIPTION OF THE FIGURES

FIG. 2: PXRD patterns of amorphous and crystalline Dasatinib glutarate

FIG. 3: PXRD patterns of amorphous and crystalline Dasatinib nicotinat

DETAILED DESCRIPTION OF THE INVENTION

Figure 1:
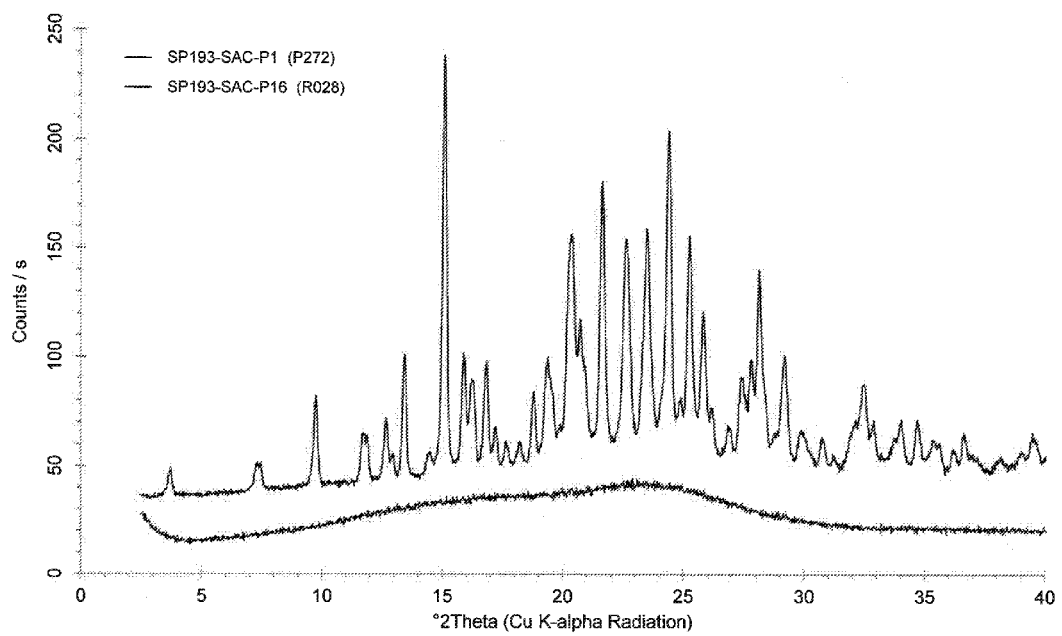
FIG. 1: PXRD patterns of amorphous and crystalline Dasatinib saccharinate

The present invention is directed to a salt of Dasatinib in amorphous form, preferably without the presence of a crystalline state, which is typically formed with a pharmaceutically acceptable acidic organic compound such as a pharmaceutically acceptable carboxylic acid or a pharmaceutically acceptable amide of a sulphonic acid. The salt of the invention thus consists mainly of Dasatinib cations and anions of the second component preferably selected from pharmaceutically acceptable carboxylic acids and amides of sulphonic acids. I.e., the salts described herein are substantially free of the crystalline form of Dasatinib or, respectively, do not contain any crystalline Dasatinib at all.

It preferably comprises less than 5 wt. %, preferably less than 3 wt. %, preferably less than 2 wt. %, preferably less than 1 wt. %, preferably less than 0.5 wt. %, preferably less than 0.1 wt. % of crystalline forms.

The acidic organic compound contained in the present amorphous salt usually is selected from the group consisting of carboxylic acids and amides of a sulphonic acids, preferably from species of this group which are solids under normal conditions (300K, atmospheric pressure). Preferably, the salt is a salt selected from the group consisting of Dasatinib nicotinate, Dasatinib glutarate and Dasatinib saccharinate.

Preferably, a salt according to the present invention comprises or consists of a cation of a compound of formula 1 (INN: Dasatinib)

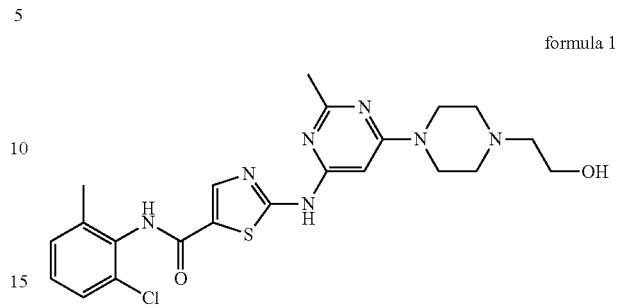

formula 1 and an anion of a second compound selected from the group consisting of glutaric acid, nicotinic acid and saccharin.

The present amorphous salt, in general, is essentially free of tectons or complexing agents such as oligo- or polysaccharides, alginic acids, pectins, beta glucan. The term "essentially free of tectons or complexing agents" means that it generally comprises less than 3 wt. %, preferably less than 2 wt. %, more preferably less than 1 wt. %, most preferably less than 0.5 wt. %, and most especially less than 0.1 wt. % of any tecton or complexing agent.

Preferably, the salt of the invention is characterized in that the molar ratio of Dasatinib to the respective organic acid (i.e. glutaric acid, nicotinic acid or saccharin) is in the range of from 0.5 to 2.0, preferably about 1:1.

As noted above, the amorphous salt of the invention, and thus the amorphous solid formed by it, mainly consists of cations of a compound of formula 1 (typically the protonated form of Dasatinib) and the second component (hereinbelow also denoted as salt former), which is generally selected from a pharmaceutically acceptable acidic organic compounds such as a carboxylic acid or an amide of a sulphonic acid (typically in the form of its deprotonated anion). The term "mainly consists of" herein denotes a content of at least 80% by weight, preferably at least 90% by weight, more preferably at least 95% by weight, and most preferably at least 99% by weight, of the compound of formula 1 and its salt former.

In a preferred embodiment, the salt according to the invention is water-soluble, wherein the solubility of the salt in water at 25° C. is greater than 0.01 mg salt per ml water, preferably greater than 0.1 mg salt per ml water, in particular greater than 1.0 mg salt per ml water, wherein the measuring is preferably performed after two hours of stirring and, respectively, equilibrating.

In a further preferred embodiment, the salt according to the present invention after storage at ambient conditions, preferably at 25° C. at 100 kPa, in a closed glass vial for a period of 8 month or more, preferably of 10 month or more, in particular of 11 month, is substantially free of the crystalline form of Dasatinib. It preferably comprises less than 5 wt. %, preferably less than 3 wt. %, preferably less than 2 wt. %, preferably less than 1 wt. %, preferably less than 0.5 wt. %, preferably less than 0.1 wt. % of crystalline forms. Further preferred, it does not contain any crystalline Dasatinib at all.

Preferably, the absence or presence, respectively, of crystalline material is determined by using X-ray Powder Diffraction (XRD).

Surprisingly, the salts according to the present invention have high glass transition temperatures, typically of more than 50° C. The high glass transition temperatures make it easier to handle the amorphous solids and increase the physical and chemical stability, thus eliminating or reducing the need for large amounts of additional components (such as polymers, stabilizers, complexing agents etc.). Further, the particles' tendency to stick together upon storage, is reduced. In a preferred embodiment, the salt according to the present invention, especially the salt selected from the group consisting of Dasatinib nicotinate, Dasatinib glutarate and Dasatinib saccharinate, has a glass transition temperature of 70° C. or more.

In a yet further preferred embodiment, the salt according to the present invention, especially Dasatinib saccharinate, has a glass transition temperature of more than 80° C. The glass transition temperature is as determined by using differential scanning calorimetry.

Another object of the invention is a process for obtaining a salt according to the invention (as described herein) comprising the steps of:

a) providing a compound of formula 1 (INN: Dasatinib)

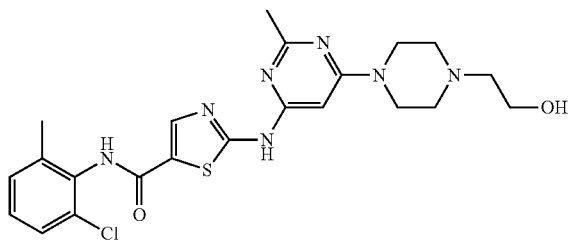

formula 1 in a suitable solvent or a mixture of solvents b) adding glutaric acid, or nicotinic acid, or saccharin to the mixture of step a);

c) optionally mixing the composition of step b) with an antisolvent (like water) and/or optionally concentrating the composition of step b);

d) optionally evaporating to dryness, e.g. by freeze-drying, spray-drying etc.

Preferably, the molar ratio of compound of formula 1 (in step a)) and the second compound (glutaric acid, or nicotinic acid, or saccharin) (in step b)) is in the range of from 0.5 to 2.0, preferably about 1:1.

Step b) usually comprises providing glutaric acid, or nicotinic acid, or saccharin in solid form, or as a solution, generally in water, an alcohol, a ketone, an acetate, or a mixture of solvents, preferably in methanol, ethanol or water, or a mixture of such suitable solvents.

Preferably, the solvent used in step a) is water or a water miscible organic solvent such as an alcohol (e.g. methanol or especially ethanol) or an aprotic polar organic solvent such as DMSO, DMF, or NMP, or mixtures thereof. Particularly preferred is the use of methanol, ethanol, water or a mixture of suitable solvents.

Solutions or suspension according to steps a) and/or b) preferably are concentrated solutions.

The concentration of Dasatinib in step a) may range from 0.1 to about 1000 mg/ml of solvents, preferably from 5 to 300 mg/ml. The concentration of glutaric acid, or nicotinic acid, or saccharin in step b) may range from 0.1 to about 500 mg/ml of solvents, preferably from 5 to 200 mg/ml.

The process is preferably carried out in the temperature range from 15-120° C. In a preferred process, steps a), b) and/or c) are carried out at a temperature in the range from 40-90° C., especially 50-90° C. Of technical importance is also a freeze-drying step d), which is typically carried out in a temperature range from −80° C. to below room temperature; freeze-drying is usually carried out without addition of further components (such as solid CO2).

Further details may be derived from the below examples (see e.g. example 1).

Salts according to the present invention (as described herein), e.g. Dasatinib glutarate or Dasatinib nicotinate, may also be obtained by a method comprising the step of providing e.g. crystalline Dasatinib glutarate or, respectively, Dasatinib nicotinate and converting the crystalline Dasatinib glutarate or, respectively, Dasatinib nicotinate to amorphous Dasatinib glutarate or, respectively, Dasatinib nicotinate (for details, see examples 2 and 3).

The salts of the present invention are generally obtained as a fine powder with typical particle size distributions with the median size between 0.1 and 100 μm, preferably between 1 and 50 μm, preferably between 1 to 10 μm. This particle size range ensures a fast dissolution profile, while retaining the favorable handling properties in the formulation process.

An important advantage of the salts of this invention is the dramatically enhanced aqueous solubility (for exemplary data, see examples 1 to 3). In general, the salts of the present invention show aqueous solubilities that are preferably at least factor of 2, preferably of 10, preferably of 50, in particular of 100, particularly preferably at least factor of 500, in particular of about 1,000 (or more), greater than the solubility of Dasatinib free base. Thus, the salts described herein preferably show aqueous solubilities greater than known crystalline forms of Dasatinib.

Furthermore, the salts according to the present invention are preferably characterized by high glass transition temperature in the dry state. Therefore, excellent kinetic stability can be expected when kept under dry conditions.

The salts of the present invention may be used in pharmaceutical compositions in the same way as other forms of Dasatinib previously known. Additionally, the present salts may be employed as intermediates or starting materials to produce the pure active ingredient.

A further aspect of the present invention is a pharmaceutical composition comprising, as active ingredient, a salt according to the present invention, preferably a salt as described herein above as being preferred, and preferably further comprising one, two, three, or more pharmaceutically acceptable carriers, and/or diluents, and/or further ingredients, in particular one, two, three, or more pharmaceutical excipients.

The amount of the salt in the composition depends on the type of formulation and the desired dosage regimen during administration time periods. The amount in each oral formulation may be from 0.1 to 300 mg, preferably from 1.0 to 250 mg, in particular from 5.0 to 200 mg. Preferably, the composition is (substantially) free of Dasatinib in crystalline form. It preferably comprises less than 5 wt. %, preferably less than 3 wt. %, preferably less than 2 wt. %, preferably less than 1 wt. %, preferably less than 0.5 wt. %, preferably less than 0.1 wt. % of crystalline forms.

Oral formulations (as preferred pharmaceutical compositions according to the present invention) may be solid formulations such as capsules, tablets, pills and troches, or a liquid suspension formulation.

The salts according to the invention may be used directly in the form of powders, granules, suspensions, or they may be combined together with other pharmaceutically acceptable ingredients in admixing the components and optionally finely divide them, and then filling capsules, composed for example from hard or soft gelatin, compressing tablets, pills or troches, or suspend in suspensions. Coatings may be applied after compression to form pills.

Pharmaceutically acceptable ingredients are well known for the various types of formulation and may be for example binders such as natural or synthetic polymers, excipients, disintegrants, lubricants, surfactants, sweetening and other flavouring agents, coating materials, preservatives, dyes, thickeners, adjuvants, antimicrobial agents and carriers for the various formulation types.

Examples for binders are gum tragacanth, acacia, starch, gelatin, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan, carragenan or hyaluronic acid.

Examples for excipients are phosphates such as dicalcium phosphate.

Examples for disintegrants are croscarmellose sodium, crospovidone, low-substituted hydroxypropyl cellulose, sodium starch glycolate or alginic acid.

Surfactants may be anionic, cationic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials are gelatin, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for solid carriers are talc, clay, microcrystalline cellulose, silica, alumina and the like.

The formulation according to the invention may also contain isotonic agents, such as sugars, buffers or sodium chloride.

The compositions of the present invention may also be formulated as effervescent tablet or powder, which can disintegrate in an aqueous environment to provide a drinking solution.

The most preferred route is oral administration. The dosages may be conveniently presented in a unit dosage form and prepared by any of the methods well-known in the art of pharmacy.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The salts of the present invention and its formulations or compositions containing the same, respectively, can be also be administered in combination with other therapeutic agents being effective to treat a given condition and/or to provide a combination therapy.

The salts of the present invention and the pharmaceutical compositions according to the invention are useful for effective treatment of disorders in connection with need of inhibiting the BCR/ABL and Src family tyrosine kinases. The salts of the present invention and the respective pharmaceutical compositions are useful in the treatment of chronic myelogenous leukemia but also advanced prostate cancer.

The salts of the present invention and the pharmaceutical compositions according to the invention can also be used in a therapeutic method for producing an Abl tyrosine kinase inhibiting effect in a mammal comprising administering to a mammal in need of such therapy.

The salts of the present invention may be used as single component or as mixtures with other solid forms.

In view of the above, the present invention also relates to salts of the present invention and pharmaceutical compositions according to the invention for use as a medicament, preferably for use in the treatment of cancer, in particular of chronic myelogenous leukemia (CML) and/or Philadelphia chromosome-positive acute lymphoblastic leukemia (Ph+ ALL).

In the following, the present invention will be described more closely by way of selected examples illustrating the invention.

Wherever noted, in the following, room temperature depicts a temperature from the range 22-25° C. and percentages are given by weight, if not indicated otherwise.

Abbreviations:
DSC differential scanning calorimetry
DMSO dimethyl sulfoxide
DMF dimethylformamide
NMP N-methyl-2-pyrrolidone
HPLC high pressure liquid chromatography
NMR nuclear magnetic resonance
TG-FTIR thermogravimetry coupled with Fourier-transformation infrared spectrometry
r.h. relative humidity (air, if not indicated otherwise)

TGA thermogravimetry
v/v volume by volume
wt. % percent by weight
PXRD powder X-ray diffraction
Instrumental:
Powder X-Ray Diffraction:

The measurements are carried out with a Bruker D8 Advance powder X-ray diffractometer using Cu Kα radiation in the Bragg-Brentano reflection geometry. Generally, the 2θ values are accurate within an error of ±0.1-0.2°. The relative peak intensities can vary considerably for different samples of the same crystalline form because of different preferred orientations of the crystals. The samples are prepared without any special treatment other than the application of slight pressure to get a flat surface. Generally, silicon single crystal sample holders of 0.1 mm, 0.5 mm or 1.0 mm depth are used. The tube voltage and current are 40 kV and 40 mA, respectively. The X-ray diffractometer is equipped with a LynxEye detector. A variable divergence slight is used with a 3° window. The step size is 0.02° 2θ with a step time of 37 seconds. The samples are rotated at 0.5 rps during the measurement.

Thermogravimetry coupled to infrared spectroscopy (TG-FTIR): Thermogravimetry coupled with FT-infrared spectroscopy is a well known method that allows to monitor the mass loss of a given sample upon heating while identifying the volatile substances by infrared spectroscopy. Therefore, TG-FTIR is a suitable method to identify solvates or hydrates.

TG-FTIR is performed on a Netzsch Thermo-Microbalance TG 209, which is coupled to a Bruker FT-IR Spectrometer Vector 22 or IFS 28. The measurements are carried out with aluminum crucibles with a micro pinhole under a nitrogen atmosphere and at a heating rate of 10° C./min over the range 25-250° C.

$^1$H-NMR:

The $^1$H-NMR spectra are recorded on a Bruker DPX 300 spectrometer. Solvent: Deuterated-DMSO Differential scanning calorimetry: DSC is carried out with a TA Instruments DSC Q2000 using hermetically sealed gold sample pans. The heating rate is 10° C. per minute. Samples are dried under nitrogen before sample pans are closed under nitrogen.

Solubility Determinations:

Solubility determinations are carried out in pure water at 25±2° C. Suspensions with about 10 mg salt in 0.5 mL water are prepared and equilibrated for two hours before the solution phase is filtered off and tested by HPLC.

HPLC:

HPLC is carried out on an Agilent 1100 HPLC chromatograph equipped with a UV-vis detection unit. The method is described by Mhaske, D. V. and Dhaneshwar, S. R. in Chromatographia 2007, 66(1/2), 95-102. The column type used is a Waters XTerra MS C18, 250×4.6 mm, 5 μm (FK-CC14). The method as referenced above is an isocratic method using an aqueous ammonium acetate/acetic acid and methanol with a ratio of 55/45. The applied flow rate is 1.0 mL per minute, the injection volume is 20 microliter and the detection wavelength is 321 nm.

Solvents: For all experiments, standard grade solvents are used.

EXAMPLES

Comparative Example 1

Preparation of Crystalline Dasatinib Saccharinate (Hydrate)

126 mg of Dasatinib (monohydrate form) and 46 mg of saccharin are suspended in 5 mL of water. The suspension is heated to 70° C. and stirred at 70° C. for 45 minutes. The mixture is allowed to cool to room temperature and stirred for 6 days at room temperature. Each day during the duration of the experiment the mixture is subjected to sonication for about one minute in a common ultrasonic bath. After six days of stirring the obtained suspension is filtered and air dried at room temperature. After drying at room temperature, the obtained solid product is characterized by powder X-ray diffraction and a PXRD pattern similar to that shown in FIG. 1 (see upper trace) showing peaks at locations as presented in Table 1 is obtained. The product is further dried at about 60° C./30 mbar for 1 hour and H-NMR spectroscopy, TG-FTIR and powder X-ray diffraction is performed. H-NMR indicates a molar ratio of Dasatinib to saccharin of 1:1 and the PXRD pattern as shown in FIG. 1 showing peaks at locations as presented in Table 1 is obtained. TG-FTIR reveals a mass loss of about 2.3% which is attributable to loss of water, so as to it can be assumed that the solid material is a crystalline hydrate.

TABLE 1

2-theta angles, d-spacings and qualitative relative intensities for Dasatinib sacharinate hydrate.

| Angle °2θ | d value [Å] | Qualitative relative intensity |
|---|---|---|
| 3.7 | 23.8 | vw |
| 7.3 | 12.1 | vw |
| 7.5 | 11.9 | vw |
| 9.7 | 9.1 | m |
| 11.7 | 7.5 | w |
| 11.9 | 7.5 | w |
| 12.7 | 7.0 | w |
| 13.4 | 6.6 | m |
| 15.1 | 5.87 | vs |
| 15.9 | 5.57 | m |
| 16.2 | 5.46 | m |
| 16.8 | 5.27 | m |
| 18.8 | 4.72 | m |
| 19.4 | 4.58 | m |
| 20.4 | 4.36 | vs |
| 20.7 | 4.29 | s |
| 20.9 | 4.25 | m |
| 21.6 | 4.11 | vs |
| 22.6 | 3.93 | vs |
| 23.5 | 3.78 | vs |
| 24.4 | 3.65 | vs |
| 24.9 | 3.58 | m |
| 25.2 | 3.52 | vs |
| 25.8 | 3.45 | s |
| 28.1 | 3.17 | s | vs = very strong,
s = strong,
m = medium,
w = weak

Example 1

Preparation of Amorphous Dasatinib Saccharinate 126.9 mg of Dasatinib (monohydrate form) and 45.9 mg of saccharin are dissolved in 10 mL of methanol at 60° C. and stirred for 0.5 hour at 60° C. The solvent is evaporated using a dry nitrogen flow at 60° C. within approximately 1.5 hours and the dried sample is held at 60° C. for one hour. The sample is cooled and stored overnight at room temperature and dried again at 50° C./approx. 30 mbar for 17 hours. About 150 mg of solid material are obtained which is characterized by H-NMR spectroscopy, DSC and powder X-diffraction. H-NMR spectroscopy indicates a molar ratio of Dasatinib to saccharin of 1:1. The powder X-ray diffraction pattern as shown in the bottom trace of FIG. 1 does not exhibit any sharp reflexes. Differential scanning calorimetry shows a small step near 130° C. that is attributable to the glass transition which is a characteristic property of an amorphous material. The ΔCp at the glass transition is about 0.4 J/g/K and no melting point with an enthalpy of fusion is found.

The aqueous solubility after two hours equilibration at 25° C. was determined at 1.33 mg/mL at the resulting pH value which was found to be 4.6.

The amorphous dasatinib saccharinate according to example 1 has been stored at room temperature in a closed glass vial for 11 months. Powder X-ray diffraction after 11 months of storage shows that no crystalline material was present in the amorphous sample. Investigation of a further sample of the same series by PXRD after 24 months of storage at room temperature shows the same result.

Comparative Example 2

Preparation of Crystalline Dasatinib Glutarate 127 mg of Dasatinib (monohydrate form) and 34 mg of glutaric acid are dissolved in 10 mL of methanol at 60° C. and stirred for 0.5 hour at 60° C. The solvent is evaporated using a dry nitrogen flow at 60° C. within approximately 2.5 hours and the dried sample is held at 60° C. for 1 hour. The sample is cooled and stored overnight at room temperature. H-NMR spectroscopy indicates a molar ratio of Dasatinib to glutaric acid of about 1:1. The solid material is further characterized by powder X-ray diffraction. The obtained PXRD pattern which is shown in FIG. 2 (see upper trace) exhibits sharp peaks. The peak locations of the PXRD pattern are listed in Table 2.

TABLE 2

2-theta angles, d-spacings and qualitative relative intensities for Dasatinib glutarate.

| Angle °2θ | d value [Å] | Qualitative relative intensity |
|---|---|---|
| 5.6 | 15.9 | m |
| 5.8 | 15.3 | m |
| 6.6 | 13.5 | w |
| 10.1 | 8.7 | w |
| 11.1 | 8.0 | m |
| 11.6 | 7.6 | m |
| 15.8 | 5.59 | vs |
| 16.7 | 5.31 | s |
| 20.9 | 4.26 | m |
| 21.3 | 4.18 | m |
| 23.3 | 3.82 | s |
| 23.5 | 3.78 | s |
| 25.2 | 3.53 | s |
| 25.7 | 3.46 | m |
| 26.9 | 3.31 | m |
| 28.4 | 3.14 | m |
| 28.7 | 3.11 | m | vs = very strong,
s = strong,
m = medium,
w = weak

Example 2

Preparation of Amorphous Dasatinib Glutarate 92 mg of sample crystalline Dasatinib glutarate according to comparative example 2 are suspended in 0.8 mL of water, sonicated for 1 minute and stirred at room temperature for 2.5 hours. Water is evaporated using a dry nitrogen flow at room temperature within 1 day. To the glassy material obtained 0.1 mL of water is added. The sample is sonicated for 1 minute and stirred at room temperature for 18 hours. The sticky mass is dried at room temperature using a dry nitrogen flow for 1 day and an amorphous material is obtained (see FIG. 2, bottom trace).

A sample of the amorphous Dasatinib glutarate according to example 2 is stored for 11 months at room temperature. Powder X-ray diffraction after 11 months of storage shows that no crystalline material is present in the amorphous sample. Investigation of a further sample of the same series by PXRD after 24 months of storage at room temperature shows the same result.

Comparative Example 3

Preparation of Crystalline Dasatinib Nicotinate 127 mg of Dasatinib (monohydrate form) and 31 mg of nicotinic acid are dissolved in 10 mL of methanol at 60° C. and stirred for 0.5 hour at 60° C. The solvent is evaporated using a dry nitrogen flow at 60° C. within approximately 2.5 hours and the dried sample is held at 60° C. for 1 hour. The sample is cooled and stored overnight at room temperature. H-NMR spectros-copy indicates a molar ratio of Dasatinib to nicotinic acid of 1:1. The solid material is further characterized by powder X-ray diffraction. The obtained PXRD pattern which is shown in the upper trace of FIG. 3 exhibits sharp peaks. The peak locations of the PXRD pattern are listed in Table 3.

TABLE 3

2-theta angles, d-spacings and qualitative relative intensities for Dasatinib nicotinate.

| Angle °2θ | d value [Å] | Qualitative relative intensity |
|---|---|---|
| 5.9 | 14.9 | m |
| 10.3 | 8.6 | vw |
| 10.5 | 8.4 | vw |
| 11.0 | 8.0 | m |
| 11.9 | 7.5 | s |
| 13.6 | 6.5 | w |
| 13.8 | 6.4 | w |
| 14.7 | 6.0 | s |
| 15.1 | 5.88 | w |
| 17.3 | 5.11 | w |
| 17.6 | 5.03 | w |
| 17.8 | 4.97 | w |
| 18.1 | 4.90 | w |
| 18.5 | 4.78 | m |
| 18.8 | 4.71 | w |
| 19.3 | 4.59 | m |
| 19.9 | 4.46 | s |
| 20.3 | 4.38 | m |
| 21.1 | 4.21 | m |
| 21.7 | 4.08 | w |
| 22.5 | 3.94 | w |
| 23.0 | 3.86 | w |
| 23.3 | 3.81 | m |
| 23.7 | 3.75 | m |
| 24.3 | 3.67 | vs |
| 25.2 | 3.54 | w |
| 25.6 | 3.47 | m |
| 25.8 | 3.45 | s |
| 26.4 | 3.38 | m |
| 26.6 | 3.34 | w |
| 26.9 | 3.31 | w |
| 27.3 | 3.26 | s |

TABLE 3-continued 2-theta angles, d-spacings and qualitative relative
intensities for Dasatinib nicotinate.

| Angle °2θ | d value [Å] | Qualitative relative intensity |
|---|---|---|
| 27.8 | 3.20 | w |
| 28.4 | 3.14 | m | vs = very strong,
s = strong,
m = medium,
w = weak

Example 3

Preparation of Amorphous Dasatinib Nicotinate 105 mg of sample crystalline Dasatinib nicotinate according to comparative example 3 are suspended in 0.8 mL of water, sonicated for 1 minute and stirred at room temperature for 2.5 hours. Water is evaporated using a dry nitrogen flow at room temperature within 1 day. To the glassy material obtained 0.1 mL of water is added. The sample is sonicated for 1 minute and stirred at room temperature for 18 hours. The product is dried at room temperature using a dry nitrogen flow for 1 day and an amorphous material is obtained (see FIG. 3, bottom trace).

A sample of amorphous Dasatinib nicotinate according to example 3 is stored for 11 months at room temperature. Powder X-ray diffraction after 11 months of storage shows that no crystalline material is present in the amorphous sample.

Example 4

Preparation of Amorphous Dasatinib Saccharinate 2.535 g of dasatinib (monohydrate form) and 0.921 g of saccharin are placed in a 22 mL Supelco vial, suspended in 10 mL of ethanol/water 1:1 v/v, sonicated for 1 minute and stirred at room temperature for 15 minutes. The slightly turbid solution is then added at room temperature to 80 mL of water in approx. 5 minutes while vigorously stirring with a magnetic stirrer. A white suspension is formed. The Supelco vial is washed with 10 mL of ethanol/water 1:1 v/v and the washing fluid is added to the white suspension. The suspension is stirred at room temperature for 2 minutes, and transferred into a 1 L glass flask. The flask is rotated while freezing the suspension in a mixture of dry ice/2-popanol in order to produce a thin film of frozen material. The material is freeze-dried overnight (vacuum about 0.4 mbar). The sample is dried at room temperature/approx. 30 mbar for 15 minutes, heated stepwise to 60° C. in approx. 1 hour and dried at 60° C./approx. 30 mbar for 30 minutes. Yield: 1.689 g. The material is characterized by H-NMR spectroscopy, DSC and powder X-diffraction. H-NMR spectroscopy indicates a molar ratio of Dasatinib to saccharin of 1:1. Powder X-ray diffraction shows that the material is amorphous. Differential scanning calorimetry shows a small step near about 113° C. that is attributable to the glass transition which is a characteristic property of an amorphous material. The ΔCp at the glass transition is about 0.6 J/(g K) and no melting point with an enthalpy of fusion is found.

BRIEF DESCRIPTION OF FIGURES

FIG. 1: PXRD patterns of amorphous and crystalline Dasatinib saccharinate

FIG. 2: PXRD patterns of amorphous and crystalline Dasatinib glutarate

FIG. 3: PXRD patterns of amorphous and crystalline Dasatinib nicotinat

The invention claimed is:

1. A salt of Dasatinib, wherein the salt is in amorphous form which further contains an organic acid wherein the molar ratio of Dasatinib to the organic acid is in the range of from 0.5 to 2.0 wherein the salt is a salt selected from the group consisting of Dasatinib saccharinate, Dasatinib glutarate, and Dasatinib nicotinate.

2. The salt according to claim 1, wherein the salt is in amorphous form, without the presence of a crystalline state.

3. The salt according to claim 1, wherein the salt comprises a cation of a compound of formula 1, which is also known as Dasatinib,

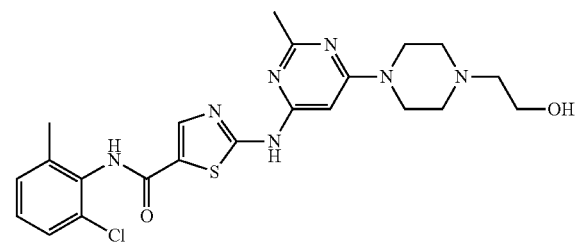

formula 1 and
an anion of a second compound selected from the group consisting of saccharin, glutaric acid, and nicotinic acid.

4. The salt according to claim 1, wherein the molar ratio of Dasatinib to the organic acid is in the range of from about 1 1.

5. The salt according to claim 1, which is essentially free of tectons or complexing agents.

6. The salt according to claim 5, comprising less than 3 wt. % of tectons or oligo- or polysaccharides, alginic acids, pectins, obeta glucan.

7. The salt according to claim 1, wherein the salt is water-soluble and wherein the solubility of the salt in water at 25° C., after equilibration for two hours, is greater than 0.01 mg salt per ml water.

8. The salt according to claim 1, wherein the salt is water-soluble and wherein the solubility of the salt in water at 25° C., after equilibration for two hours, is greater than 1.0 mg salt per ml water.

9. The salt according to claim 1, wherein the salt after storage at ambient conditions in a closed glass vial for a period of 8 months or more, and is substantially free of the crystalline form of Dasatinib as determined by X-ray Powder Diffraction (XRD).

10. The salt according to claim 1, wherein the salt after storage at ambient conditions in a closed glass vial for a period of 11 months, and is substantially free of the crystalline form of Dasatinib as determined by X-ray Powder Diffraction (XRD).

11. The salt according to claim 1, wherein the salt has a glass transition temperature of 50° C. or more as determined by differential scanning calorimetry.

12. A pharmaceutical composition comprising an active ingredient, wherein the active ingredient comprises the salt according to claim 1, and further comprising one, two, three, or more pharmaceutically acceptable carriers, and/or diluents, and/or further ingredients.

13. The pharmaceutical composition according to claim 12, wherein the total amount of amorphous Dasatinib salt in the composition is in the range of from 0.1 to 300 mg.

14. A treatment of cancer which comprises administering the pharmaceutical composition according to claim 12, as a medicament to a mammal having chronic myelogenous leukemia (CML) and/or Philadelphia chromosome-positive acute lymphoblastic leukemia (Ph+ALL) or prostate cancer.

15. A process for obtaining the salt according to claim 1, comprising the steps of:

a) providing a compound of formula 1 (INN: Dasatinib)

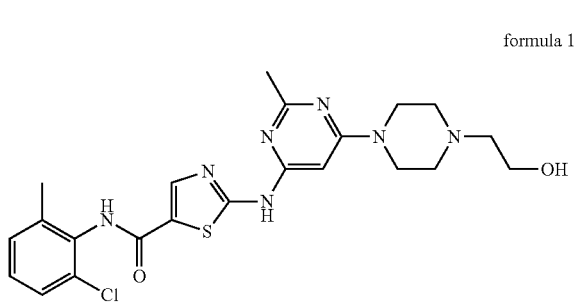 [SMILES: Cc1nc(Nc2ncc(C(=O)Nc3c(C)cccc3Cl)s2)cc(N2CCN(CCO)CC2)n1]

formula 1 in a solvent or a mixture of solvents
b) adding glutaric acid, or nicotinic acid, or saccharin, to the mixture of step a);
c) optionally mixing the composition of step b) with an antisolvent, and/or optionally concentrating the composition of step b);
d) optionally evaporating to dryness.

16. The process according to claim 15, wherein the solvent or mixture of solvents is water, alcohols and mixtures thereof, and the mixture obtained in step b) is heated to a temperature from the range 30-90° C.

17. The salt according to claim 1, wherein the salt after storage at ambient conditions in a closed glass vial for a period of 11 months or more, and does not contain any crystalline Dasatinib as determined by X-ray Powder Diffraction (XRD).

18. A process for obtaining the salt according to claim 1, comprising the steps of a) providing a compound of formula 1 (INN: Dasatinib)

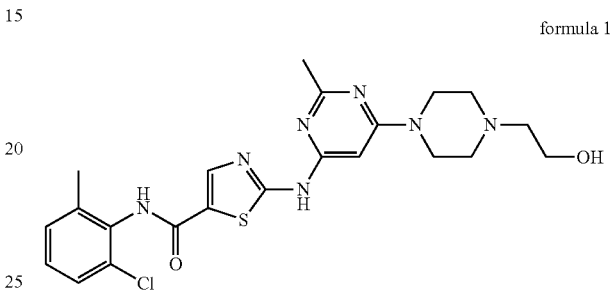

formula 1 in a solvent or a mixture of solvents
b) adding saccharin, to the mixture of step a);
c) mixing the composition of step b) with water, and/or optionally concentrating the composition of step b); and
d) evaporating to dryness.

* * * * *